United States Patent [19]

Böshagen et al.

[11] 4,328,233

[45] May 4, 1982

[54] α-GLUCOSIDASE INHIBITING 2-HYDROXYMETHYL-3,4,5-TRIHYDROXY-PIPERIDINES

[75] Inventors: Horst Böshagen, Haan; Rüdiger Sitt; Ernst Truscheit, both of Wuppertal, all of Fed. Rep. of Germany

[73] Assignee: Bayer Aktiengesellschaft, Leverkusen, Fed. Rep. of Germany

[21] Appl. No.: 88,990

[22] Filed: Oct. 29, 1979

[30] Foreign Application Priority Data

Nov. 6, 1978 [DE] Fed. Rep. of Germany ....... 2848117

[51] Int. Cl.$^3$ .................. A61K 31/445; C07D 211/46
[52] U.S. Cl. .................................... 424/267; 544/129; 544/360; 546/14; 546/203; 546/205; 546/206; 546/207; 546/210; 546/219; 546/220; 546/242
[58] Field of Search ............... 546/242, 219, 203, 205, 546/207, 210, 206, 220; 424/267; 544/129, 360

[56] References Cited

U.S. PATENT DOCUMENTS 4,065,562 12/1977 Ohata et al. ......................... 424/267
4,182,767 1/1980 Murai et al. .................... 546/242 X

OTHER PUBLICATIONS

March, J., *Advanced Organic Chemistry,* McGraw Hill, New York, 1968, pp. 509 and 689–690.
Mcomie, J., *Protective Groups in Organic Chemistry,* Plenum Press, London, 1973, pp. 103–104.

*Primary Examiner*—Richard A. Schwartz
*Attorney, Agent, or Firm*—Sprung, Horn, Kramer & Woods

[57] ABSTRACT

The invention relates to 2-hydroxymethyl-3,4,5-trihydroxy-6-substituted-piperidines and methods for their preparation. The invention also includes compositions containing said 2-hydroxymethyl-3,4,5-trihydroxy-6-substituted-piperidines and the use of said compounds and compositions for influencing carbohydrate metabolism and fat metabolism and for use in animal nutrition as feed additives.

22 Claims, No Drawings

α-GLUCOSIDASE INHIBITING 2-HYDROXYMETHYL-3,4,5-TRIHYDROXY-PIPERIDINES

The invention relates to new 2-hydroxymethyl-3,4,5-trihydroxy-piperdine compounds, to a process for their production and to their use as medicaments for influencing carbohydrate metabolism and fat metabolism and to their use in animal nutrition as feed additives.

According to the present invention there are provided compounds of the general formula

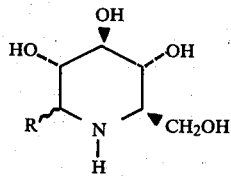

in which R denotes an optionally substituted straight-chain, branched or cyclic saturated or unsaturated aliphatic hydrocarbon radical which is optionally interrupted by one or more hetero-atoms, e.g. O or S, an optionally substituted aromatic radical or an optionally substituted heterocyclic radical.

R preferably denotes $C_1$ to $C_{30}$ alkyl, $C_2$ to $C_{18}$ alkenyl, $C_2$ to $C_{18}$ alkinyl, $C_3$ to $C_{12}$ cycloalkyl, $C_3$ to $C_{12}$ cycloalkenyl, $C_5$ to $C_{12}$ cycloalkadienyl, $C_7$ to $C_{12}$ bicycloalkyl, $C_7$ to $C_{12}$ bicycloalkenyl, $C_7$ to $C_{12}$ bicycloalkadienyl, $C_8$ to $C_{12}$ tricycloalkyl, $C_8$ to $C_{12}$ tricycloalkenyl or $C_8$ to $C_{12}$ tricycloalkadienyl, phenyl, naphthyl or $C_3$ to $C_7$ heterocyclyl with 1 to 4 hetero-atoms selected from N, O and S, onto which a benzene radical can be fused, it being possible for the radicals listed to carry 1 to 5 (preferably 1 to 3 and more preferably 1 or 2) substituents.

Preferred substituents of phenyl, naphthyl and heterocyclyl are halogen, preferably chlorine, bromine or fluorine, $C_1$ to $C_4$ alkyl, halogeno-$C_1$ to $C_4$ alkyl, $C_1$ to $C_4$ alkoxy, $C_1$ to $C_4$ alkylmercapto, $C_1$ to $C_4$ alkylsulphonyl, nitro, cyano, di-$C_1$ to $C_{12}$ alkylamino, di-$C_1$ to $C_{12}$ alkylaminosulphonyl, di-$C_1$ to $C_{12}$ dialkylaminocarbonyl, pyrrolidino, pyrrolidinosulphonyl, pyrrolidinocarbonyl, piperidino, piperidinosulphonyl, piperidinocarbonyl, morpholino, morpholinsulphonyl, morpholinocarbonyl, N'-$C_1$ to $C_4$ alkylpiperazino, N'-$C_1$ to $C_4$ alkylpiperazinosulphonyl, N'-$C_1$ to $C_4$ alkylpiperazinocarbonyl, pyridyl, thienyl, imidazolyl, isoxazolyl, thiazolyl, glucopyranosyl and ribofuranosyl. Thus, for example, phenyl or naphthyl may be substituted by halogen, $C_1$-$C_4$-alkyl, halogeno-$C_1$-$C_4$-alkyl, $C_1$-$C_4$-alkoxy, $C_1$-$C_4$-alkylmercapto, $C_1$-$C_4$-alkylsulphonyl, nitro, cyano, di-$C_1$ to $C_{12}$ alkylamino, di-$C_1$ to $C_{12}$ alkylaminosulphonyl or di-$C_1$ to $C_{12}$ dialkylaminocarbonyl.

Examples which may be mentioned of substituents on the remaining radicals R are $C_1$ to $C_4$ alkyl, $C_1$ to $C_4$ alkoxy, $C_1$ to $C_4$ alkylmercapto, halogen, e.g. fluorine, chlorine and bromine, di-$C_1$ to $C_{12}$ alkylamino, pyrrolidino, piperidino, morpholino, N'-$C_1$ to $C_4$ alkylpiperazino or phenyl or naphthyl which is optionally substituted by halogen, in particular fluorine, chlorine and bromine, $C_1$ to $C_4$ alkyl, $C_1$ to $C_4$ alkoxy, $C_1$ to $C_4$ alkylmercapto, $C_1$ to $C_4$ alkylsulphonyl, nitro, $C_1$ to $C_4$ alkoxycarbonyl, di-$C_1$ to $C_{12}$ alkylaminocarbonyl, di-$C_1$ to $C_4$ alkylaminosulphonyl, pyridyl, thienyl, imidazolyl, isoxazolyl, thioazolyl, glucopyranosyl and ribofuranosyl. Thus, for example, when R is $C_1$ to $C_{30}$ alkyl, $C_2$ to $C_{18}$ alkenyl or $C_2$ to $C_{18}$ alkinyl, it may be substituted by halogen, $C_1$-$C_4$-alkoxy or nitro.

The alkyl radicals R can furthermore carry $C_3$ to $C_{12}$ cycloalkyl, $C_3$ to $C_{12}$ cycloalkenyl, $C_5$ to $C_{12}$ cycloalkadienyl, $C_7$ to $C_{12}$ bicycloalkyl, $C_7$ to $C_{12}$ bicycloalkenyl, $C_7$ to $C_{12}$ bicycloalkadienyl, $C_8$ to $C_{12}$ tricycloalkyl, $C_8$ to $C_{12}$ tricycloalkenyl or $C_8$ to $C_{12}$ tricycloalkadienyl as substituents.

In preferred compounds of the formula (I), R denotes a $C_1$ to $C_{18}$ alkyl radical, optionally substituted by 1 to 5 halogen atoms, a $C_3$ to $C_{10}$ alkenyl, a $C_3$ to $C_{10}$ alkinyl or $C_3$ to $C_7$ cycloalkyl radical or a phenyl radical which is optionally substituted by halogen, $C_1$ to $C_4$-alkyl, $C_1$ to $C_4$ alkoxy or nitro.

According to the present invention there is further provided a process for the production of compounds of the present invention in which 2-hydroxymethyl-3,4,5-trihydroxy-6-cyanopiperidine is silylated on the OH groups by warming, with the addition of a catalyst, with a hexaalkyl-disilazane or a trialkylsilicon halide, alkyl preferably being $C_1$ to $C_4$ alkyl and halogen preferably being chlorine, hexamethyldisilazane being preferred and the product is reacted with an organometallic reagent of the general formula

in which R has the abovementioned meaning and Y denotes a metal or halogeno-metal, and the silyl protective groups are split off.

A mixture which can be separated, of the α-compound and β-compound is obtained, the α-derivative predominating. The efficacies of the α- and β-form differ only less; the α-form is in general a little more efficacious.

The compound which has the lower Rf value in the running agent ethyl acetate/methanol/water/$NH_4OH$ (100/60/25/1) on Merck TLC pre-coated plates, silica gel 60 F 254, is designated the α-form.

As can be seen from the following equation, the cyano group is surprisingly substituted by the particular alkyl radical intended in a chemically unusual process, the active α-form being obtained in a considerably higher yield than the β-form. Aromatisation to give the pyridine derivative does not occur. Suitable catalysts for the silylation are imidazole and 1,2,4-triazole. The separation of the α- and β-forms is performed with cationic exchange resins, e.g. Dowex 50 WX 4.

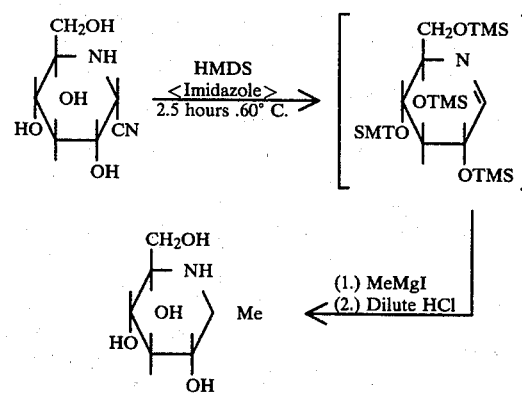

The reaction with hexamethyldisilazane takes place with the addition of imidazole (~0.1 mol equivalent) at a temperature of 20°–125° C., preferably 60° C., in the course of 2–18 hours, an excess of hexamethyldisilazane simultaneously serving as the solvent. Excess hexamethyldisilazane is then stripped off in vacuo and the residue is dissolved in an inert solvent, preferably diethyl ether, and reacted with an organometallic reagent, dissolved in an inert solvent, for example ether, petroleum ether or ligroin, at a temperature of 20°–60° C., preferably at room temperature. The silyl groups are then removed by treating the reaction solution with dilute hydrochloric acid (preferably 1 N HCl) at room temperature for 18 hours. The aqueous phase is separated off, neutralized with sodium hydroxide solution and evaporated. The crude product thus obtained is freed from concomitant salts by means of a cation exchanger and is then further purified in a suitable manner.

2-Hydroxymethyl-3,4,5-trihydroxy-6-cyanopiperidine is prepared from 5-amino-5-desoxy-D-glucose-1-sulphonic acid (S. Inouye et al., Tetrahedron 23, 2143 (1968)) and hydrocyanic acid analogously to the preparation of 2,6-imino-2-hydroxymethyl-2,6-didesoxy-L-ido-hexonic acid nitril (H. Paulsen et al., Chem. Ber. 100, 812 (1967)).

The organometallic compounds employed are known and are preferably alkyl (particularly $C_1$–$C_{12}$ alkyl), alkenyl or alkinyl (particularly $C_2$–$C_{12}$ alkenyl or alkinyl) cycloalkyl or cycloalkenyl (particularly having 5 to 7 ring members) or phenyl-methyl or ethyl magnesium halides (preferably chlorides or bromides) or the corresponding organolithium compounds. Examples which may be mentioned are n-nonyl-magnesium bromide, undec-2-yl-magnesium bromide, 2-methyl-but-2-yl-magnesium chloride, cyclobutyl-magnesium bromide, cycloheptyl-magnesium bromide, vinyl-magnesium bromide, propenyl-magnesium bromide, benzyl-magnesium chloride, allyl-magnesium bromide, propargyl-magnesium bromide, cyclopent-1-enyl-magnesium bromide, [6,6-dimethyl-bicyclo[3,1,1]heptan-2-yl]-methyl-magnesium chloride, myrtenyl-magnesium chloride, 3-chloromagnesium-tricyclo[2,2,1,0$^{2,6}$]heptane, 3-diethylamino-propyl-magnesium chloride, methyl-1,3-dioxolan-2-yl-propyl-magnesium chloride and 2,4-dimethyl-1,3-thiazol-5-yl-magnesium iodide, or organolithium equivalents thereof.

It has been found that the new compounds of the present invention are potent inhibitors for α-glucosidases, in particular for disaccharidases (as for example intestinal saccharase (sucrase), maltase, isomaltase and glucoamylase). The new compounds are hence valuable agents for influencing a number of metabolism processes, and thus enrich the range of medicaments. In contrast with 2-hydroxymethyl-3,4,5-trihydroxypiperidine, which is known from DT-OS (German Published Specification) No. 2,656,602, the new compounds have advantageous therapeutic properties.

The inhibitors according to the invention are suitable as therapeutic agents for the following applications: obesity, diabetes and hyperlipoproteinemia.

To broaden the action spectrum, it can be advantageous to combine inhibitors for glycoside hydrolases which complement one another in their action, the combinations being either combinations of the inhibitors according to the invention with one another or combinations of the inhibitors according to the invention with inhibitors which are already known. Thus, for example, it can be advantageous to combine saccharase inhibitors according to the invention with amylase inhibitors which are already known.

In some cases, combinations of the inhibitors according to the invention with known oral antidiabetic agents (β-cytotropic sulphonylurea derivatives and/or biguanides having an action on the blood sugar) and with active compounds which lower the blood lipid level, such as clofibrate, nicotinic acid and cholestyramine are also advantageous.

The compounds can be administered without dilution, for example as powders or in a gelatine casing, or in combination with an excipient in a pharmaceutical composition.

The present invention thus provides a pharmaceutical composition containing as active ingredient from 0.1 to 99.5% of a compound of the invention in admixture with a solid or liquefied gaseous diluent, or in admixture with a liquid diluent other than a solvent of a molecular weight less than 200 (preferably less than 350 except in the presence of a surface active agent i.e. in admixture with a solid, liquid or liquefied gaseous diluent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once, or for example, twice, three times or four times a day respectively, usually being administered at all main meal times and secondary meal times daily.

Other therapeutic agents can also be taken. Although the dosage scheme should be carefully balanced in each case, applying well-founded professional judgment and taking into account the age, the weight and the condition of the patient and the nature and severity of the disease, the dosage will usually be in a range between about 0,5 and 200 mg/kg of the body weight per day. In some cases an adequate therapeutic effect will be achieved with a relatively small dose, whilst in other cases a larger dose will be required.

Oral administration can be carried out using solid and liquid dosage units, for example in the form of powders tablets, dragees, capsules, granules, suspensions and solutions.

A powder is prepared by comminuting the substance to a suitable size and mixing it with a pharmaceutical excipient which is likewise comminuted. Although an edible carbohydrate, such as, for example, starch, lactose, sucrose or glucose is usually used for this purpose and can also be used in this case, it is desirable to use a non-metabolising carbohydrate such as, for example, a cellulose derivative.

Sweeteners, flavouring additives, preservatives, dispersing agents and colouring agents can also be co-used.

The capsules can be produced by preparing the powder mixture described above and by filling gelatine casings which have already been formed. Before the filling operation lubricants, such as, for example, silica gel, talc, magnesium stearate, calcium stearate or solid polyethylene glycol, can be added to the powder mixture. A disintegrator or solubilising agent, such as, for example, agar-agar, calcium carbonate or sodium carbonate, can likewise be added to the mixture in order to improve the accessibility of the inhibitor when the capsule is taken.

Tablets are produced, for example, be preparing a powder mixture, of coarse or fine grain size, and adding a lubricant and disintegrator. Tablets are formed from this mixture. A powder mixture is prepared by mixing the substance, which has been comminuted in a suitable manner, and making up with a diluent or another excipient, as described above. Further substances which are added if appropriate are a binder: for example carboxymethylcellulose, alginates, gelatine or polyvinylpyrrolidones, a solution retarder, such as, for example, paraffin, a resorption accelerator, such as, for example, a quaternary salt, and/or an adsorbent, such as, for example, bentonite, kaolin or dicalcium phosphate. The powder mixture can be granulated, together with a binder, such as, for example, syrup, starch paste or acacia mucillage, or solutions of cellulose materials or polymeric materials. The product is then pressed through a coarse sieve. As an alternative to this, the powder mixture can be allowed to run through a tabletting machine and the resulting pieces of non-uniform shape can be comminuted down to a particle size. A lubricant, such as, for example, stearic acid, a stearate salt, talc or mineral oil, can be added to the resulting particles so that these do not stick in the tablet-forming nozzles. This mixture, which has been given slip properties, is then pressed into tablet form. The active compounds can also be combined with free-flowing inert excipients and brought direct into tablet form omitting the granulating or fragmentation steps. The product can be provided with a clear or opaque protective shell, for example a coating of shellac, a coating of sugar or polymeric substances and a polished shell of wax. Dyestuffs can be added to these coatings so that the different dosage units can be differentiated.

The formulation forms to be administered orally, such as, for example, solutions, syrups and elixirs, can be prepared in dosage units, so that a specific amount of the formulation contains a specific amount of active compound. A syrup can be prepared by dissolving the active compound in an aqueous solution which contains suitable flavouring agents; elixirs are obtained using non-toxic, alcoholic excipients. Suspensions can be prepared by dispersing the compound in a non-toxic excipient. Solubilising agents and emulsifying agents, such as, for example, ethoxylated isostearyl alcohols and polyoxyethylenesorbitol esters, preservatives, flavour-improving additives, such as, for example, peppermint oil or saccharin, and the like can also be added.

Dosage instructions can be indicated on the capsule. In addition, it is possible to safeguard the dosage by releasing the active compound in a delayed manner, for example by enclosing the active compound in polymer substances, waxes or the like.

In addition to the above-mentioned pharmaceutical compositions, foodstuffs containing these active compounds can also be prepared; for example sugar, bread, potato products, fruit juice, beer, chocolate and other confectionery, and preservatives, such as, for example, jam, and in this case a therapeutically effective amount of a least one of the inhibitors according to the invention is added to these products.

The food-stuffs produced using the active compounds according to the invention are suitable both for the diet of warm-blooded animals suffering from metabolism disorders and for the nutrition of healthy animals in the sense which prevents metabolism disorders.

The compounds according to the invention furthermore have the property of influencing to a great extent the relationship between the proportion of undesired fat to the proportion of desired meat of low fat content (lean meat) in animals in favour of the lean meat. This is of particular importance for rearing and keeping agricultural livestock, for example, in the fattening of pigs, but is also of considerable importance for rearing and keeping other livestock and pets. Using the inhibitors can furthermore lead to a considerable rationalisation of feeding of animals, from the point of view of time, quantity and quality. Since the inhibitors cause a certain delay in digestion, the residence time of the nutrients in the digestive tract is extended and this makes possible ad libitum feeding, which is associated with a low expenditure. Moreover, using the inhibitors according to the invention in many cases results in a considerable saving of valuable protein feed.

The active compounds can thus be used in virtually all fields of animal nutrition as agents for reducing the deposition of fat and for saving feed protein.

Accordingly the present invention provides a medicated feed comprising a compound of the present invention and a nutritious material.

The activity of the active compounds is largely independent of the species and sex of the animals. The active compounds prove particularly valuable in the case of species of animals which, generally or at certain periods of their life, tend to deposit relatively large amounts of fat.

The following livestock and pets may be mentioned as examples of animals for which the inhibitors can be employed for reducing the deposition of fat and/or for saving feed protein: warm-blooded animals, such as cattle, pigs, horses, sheep, goats, cats, dogs, rabbits, fur-bearing animals, for example mink and chinchillas, other pets, for example guinea pigs and hamsters, laboratory animals and zoo animals, for example rats, mice, apes and the like, and poultry, for example broilers, hens, geese, ducks, turkeys, pigeons, parrots and canaries, and cold-blooded animals, such as fish, for example carp, and reptiles, for example snakes.

Because of the favourable properties of the active compounds, the amount of the active compounds which is administered to the animals to achieve the desired effect can be varied substantially. It is preferably about 0.5 mg to 2.5 g and in particular 10 to 100 mg/kg of feed per day. The period of administration can be from a few hours or days up to several years. The appropriate amount of active compound and the appropriate period of administration are closely related to the aim of feeding. They depend, in particular on the species, age, sex, state of health and nature of keeping of the animals and can easily be determined by any expert.

The active compounds according to the invention are administered to the animals by the customary methods. The nature of the administration depends, in particular, on the species, the behaviour and the general condition of the animals. Thus, administration can be effected orally once or several times daily at regular or irregular intervals. For reasons of expediency, in most cases oral administration, in particular in the rhythm of the intake of food and/or drink by the animals, is to be preferred.

The active compounds can be administered as pure substances or in the formulated form, the formulated form being understood as a premix, that is to say as a mixture with non-toxic inert carriers of any desired nature, as a part of a total ration in the form of a supplementary feed or as a mixing component of a mixed feed for use by itself. Administration of suitable formulations via the drinking water is also included.

The active compounds, optionally in the formulated form, can also be administered in a suitable form together with other nutrients and active compounds, for example mineral salts, trace elements, vitamins, proteins, energy carriers (for example starch sugars, fats), dyestuffs and/or flavouring agents or other feed additives, such as, for example, growth promoters. The active compounds can be administered to the animals before, during or after intake of the feed.

Oral administration together with the feed and/or drinking water is recommended, the active compounds being added to all or only part of the feed and/or drinking water as required.

The active compounds can be admixed to the feed and/or drinking water in accordance with customary methods by simple mixing as pure substances, preferably in the finely divided form or in the formulated form mixed with edible, non-toxic carriers, and optionally also in the form of a premix or a feed concentrate.

The feed and/or drinking water can contain the active compounds according to the invention in a concentration of, for example, about 0.001 to 5.0%, in particular 0.02 to 2.0% (by weight). The optimum level of the concentration of the active compound in the feed and/or drinking water depends in particular, on the amount of feed and/or drinking water taken in by the animals and can easily be determined by any expert.

The nature of the feed and its composition is irrelevant in this context. All the customary, commercially available or specific feed compositions, which preferably contain the customary equilibrium of energy substances and proteins, including vitamins and mineral substances, necessary for balanced nutrition, can be used. The feed can be composed, for example, of vegetable substances, for example shredded oilcake, shredded cereal and cereal by-products, and also hay, silage fodder, beet and other forage plants, of animal substances, for example meat products and fish products, bone meal, fats, vitamins, for example A, D, E, K and B complex, and specific sources of protein, for example yeasts, and certain aminoacids and mineral substances and trace elements, such as, for example, phosphorus and iron, zinc, manganese, copper, cobalt, iodine and the like.

Premixes can preferably contain about 0.1 to 50%, in particular 0.5 to 5.0% (by weight) of compounds according to the invention, in addition to any desired edible carriers and/or mineral salts, for example carbonated feed lime, and are prepared by the customary mixing methods.

Mixed feeds preferably contain 0.001 to 5.0%, in particular 0.02 to 2.0% (by weight) of compounds according to the invention, in addition to the customary raw material components of a mixed feed, for example, shredded cereal or cereal by-products, shredded oilcake, animal protein, minerals, trace elements and vitamins. They can be prepared by the customary mixing methods.

In premixes and mixed feedstuffs, preferably, the active compounds can also optionally be protected from air, light and/or moisture by suitable agents which coat their surface, for example with non-toxic waves or gelatine.

The following is an example of the composition of a finished mixed feed for poultry, which contains an active compound according to the invention: 200 g of wheat, 340 g of maize, 360.3 g of coarse soya bean meal, 60 g of beef tallow, 15 g of dicalcium phosphate, 10 g of calcium carbonate, 4 g of iodonated sodium chloride, 7.5 g of a vitamin/mineral mixture and 3.2 g of an active compound premix give, after careful mixing, 1 kg of feed.

The vitamin/mineral mixture consists of: 6,000 I.U. of vitamin A, 1,000 I.U. of vitamin $D_3$, 10 mg of vitamin E, 1 mg of vitamin $K_3$, 3 mg of riboflavin, 2 mg of pyridoxine, 20 mg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$. The active compound premix contains, for example, the compound according to Example 1 in the desired amount, for example 1,600 mg, and in addition 1 g of DL-methionine as well as an amount of soya bean meal such that 3.2 g of premix are formed.

The following is an example of the composition of a mixed feed for pigs, which contains an active compound of the formula (I): 630 g of shredded cereal feed (composed of 200 g of shredded maize, 150 g of shredded barley, 150 g of shredded oats and 130 g of shredded wheat), 80 g of fish meal, 60 g of coarse soya bean meal, 58.8 g of tapioca meal, 38 g of brewer's yeast, 50 g of a vitamin/mineral mixture for pigs (composition, for example, as for the chick feed), 30 g of linseed cake meal, 30 g of maize gluten feed, 10 g of soya bean oil, 10 g of sugarcane molasses and 2 g of an active compound premix (composition, for example, as for the chick feed) give, after careful mixing, 1 kg of feed.

The feed mixtures indicated are intended preferably for rearing and fattening chicks and pigs respectively, but they can also be used, in the same or a similar composition, for rearing and fattening other animals.

The inhibitors can be used individually or in any desired mixtures with one another.

IN VITRO SACCHARASE INHIBITION TEST

The in vitro saccharase inhibition test makes it possible to determine the inhibitory activity of a substance on enzymes by comparing the activity of solubilised intestinal disaccharidase complex in the presence and in the absence (so-called 100% value) of the inhibitor. A virtually glucose-free sucrose (glucose < 100 ppm) is used as the substrate which determines the specificity of the inhibition test; the determination of the enzyme activity is based on the spectrophotometric determination of liberated glucose by means of glucose dehydrogenase and nicotinamide-adenine dinucleotide as the cofactor.

A saccharase inhibitor unit (SIU) is defined as the inhibitory activity which reduces a given saccharolytic activity in a defined test batch by one unit (saccharase unit=SU); the saccharase unit is thereby defined as the enzyme activity which, under the given conditions, splits one $\mu$mol of sucrose per minute and thus leads to the liberation of one μmol each glucose, which is determined in the test, and fructose, which is not recorded in the test.

The intestinal disaccharidase complex is obtained from swine small intestine mucosa by tryptic digestion, precipitation from 66% strength ethanol at −20° C., taking up the precipitate in 100 mM phosphate buffer of pH 7.0 and finally dialysis against the same buffer.

100 μl of a dilution of the intestinal disaccharidase complex in 0.1 M maleate buffer of pH 6.25 are added to 10 μl of a sample solution which is made up of such that the extinction of the test batch is at least 10%, but not more than 25%, below that of the 100% value, and the mixture is pre-incubated at 37° C. for 10 minutes. The dilution of the disaccharidase complex is to be adjusted to an activity of 0.1 SIU/ml.

The saccharolytic reaction is then started by adding 100 μl of a 0.4 M solution of sucrose ("Serva 35779") in 0.1 M maleate buffer of pH 6.25 and, after an incubation period of 20 minutes at 37° C., is stopped by adding 1 ml of glucose dehydrogenase reagent (1 small bottle of a lyophilised glucose dehydrogenase/mutarotase mixture ("Merck 14053") and 331.7 mg of β-nicotinamide-adenine dinucleotide (free acid, "Boehringer", degree of purity I) dissolved in 250 ml of 0.5 M tris buffer of pH 7.6). To determine the glucose, the mixture is incubated at 37° C. for 30 minutes and finally measured photometrically at 340 nm against a reagent blank (with the enzyme but without sucrose).

Calculation of the inhibitory activity of inhibitors is made difficult by the fact that even slight changes in the test system, for example a 100% value which varies slightly from determination to determination, have an influence on the test result which can no longer be ignored. These difficulties are by-passed by running a standard with each determination; a saccharase inhibitor of the formula $C_{25}H_{43}O_{18}N$ which has a specific inhibitory activity of 77,700 SIU/g and, when employed in the test in amounts of 10 to 20 mg, leads to an inhibition of the order of size specified above, is used as the standard. When the difference in the extinctions at 340 nm between the 100% value and the batch inhibited by the standard is known, it is possible to calculate the specific inhibitory activity of the inhibitor, expressed in saccharase inhibitor units per gram (SIU/g), in a known manner from the difference in extinction between the 100% value and the batch inhibited by the example solution, taking into consideration the amount of inhibitor employed.

The Rf values for thin layer chromatography indicated in the following examples were determined on Merck TLC pre-coated plates, silica gel 60 F 254, eluting agent: ethyl acetate/methanol/water/NH$_4$OH: 100/60/25/1; detection: 1% strength aqueous KMnO solution.

The following Examples illustrate the preparation of compounds of the invention.

EXAMPLE 1

2-Hydroxymethyl-3,4,5-trihydroxy-6-methyl-piperidine 3.8 g (20 mmols) of 2-hydroxymethyl-3,4,5-trihydroxy-6-cyano-piperidine are suspended in 20 ml of hexamethyldisilazane, and 0.3 g of imidazole is added. The mixture is then warmed to 60° C. for 2.5 hours, whilst stirring. The clear solution is evaporated in vacuo, the residue is taken up in 100 ml of absolute diethyl ether, and 50 mmols (∼75 ml) of an ethereal-methyl-magnesium iodide solution are added dropwise, whilst stirring. A precipitate thereby forms. The mixture is stirred at room temperature for a further 2 hours. 250 ml of ice-water and 10 ml of concentrated hydrochloric acid are added and the mixture is stirred at room temperature for a further 18 hours. The aqueous phase is then separated off, neutralised with dilute sodium hydroxide solution and evaporated in vacuo. The syrup obtained is taken up in methanol, the insoluble salts is seperated off and the filtrate is evaporated again in vacuo. This procedure is repeated and gives 6–10 g of syrup. The syrup is dissolved in 50 ml of water and discharged onto a Dowex 50 W×4 (H+ form) exchanger column ($\phi$=2.5 cm, L=30 cm). The column is first washed with 1.0 l of water and then eluted with 2% strength ammonia solution. 2.8 g of crude product (mixture of the α-form and β-form) are obtained. The ion exchanger separation is repeated, the column being eluted with 0.1% strength ammonia. 0.1 g of the β-form is first isolated as a non-crystalline resin, and then 2.3 g of the crystalline α-form (that is to say 69% of theory), which melts at 172° C. after recrystallisation from methanol, are isolated;

thin layer chromatography:

Merck TLC pre-coated plates, silica gel 60F 254 eluting agent: ethyl acetate/methanol/water/N-H$_4$OH=100/60/25/1 detection: 1% strength aqueous KMnO$_4$ solution

Rf=0.25

The following comounds are obtained in an analogous manner with the aid of the appropriate organometallic compounds.

EXAMPLE 2

2-Hydroxymethyl-3,4,5-trihydroxy-6-ethyl-piperidine 0.1 g of the β-form and 2.2 g (57% of theory) of the α-form, as colourless crystals of melting point 160° C., are obtained from 3.8 g of 2-hydroxymethyl-3,4,5-trihydroxy-6-cyanopiperidine; $R_f$=0.47. (For the conditions, see Example 1).

EXAMPLE 3

2-Hydroxymethyl-3,4,5-trihydroxy-6-propyl-piperidine 0.6 g of the β-form ($R_f$=0.6) and 2.7 g (that is to say 65% of theory) of the α-form, as a colourless syrup, are obtained from 3.8 g of 2-hydroxymethyl-3,4,5-trihydroxy-6-cyanopiperidine.

MS=174 m/e (M—CH$_2$OH)

$R_f$=0.40 (for the conditions, see Example 1).

EXAMPLE 4

2-Hydroxymethyl-3,4,5-trihydroxy-6-n-butyl-piperidine 2.0 g (45% of theory) of the crystalline α-form are obtained from 3.8 g of 2-hydroxymethyl-3,4,5-trihydroxy-6-cyanopiperidine. Recrystallisation from cyclohexane gives colourless prisms of melting point 143° C.; $R_f$=0.55. (For the conditions, see Example 1).

EXAMPLE 5

2-Hydroxymethyl-3,4,5-trihydroxy-6-n-pentyl-piperidine 0.8 g (17% of theory) of the α-form are obtained as a colourless syrup from 3.8 g of 2-hydroxymethyl-3,4,5-trihydroxy-6-cyanopiperidine.

MS=202 m/e (M—CH$_2$OH)

$R_f$=0.72 (for the conditions see Example 1).

EXAMPLE 6

2-Hydroxymethyl-3,4,5-trihydroxy-6-n-octyl-piperidine 2.3 g (41% of theory) of the crystalline α-form are obtained from 3.8 g of 2-hydroxymethyl-3,4,5-trihydroxy-6-cyanopiperidine. Recrystallisation from methanol gives small colourless needles of melting point 122° C.; $R_f$=0.91. (For the conditions, see Example 1).

EXAMPLE 7

2-Hydroxymethyl-3,4,5-trihydroxy-6-phenyl-piperidine 1.3 g (27% of theory) of the α-form are obtained from 3.8 g of 2-hydroxymethyl-3,4,5-trihydroxy-6-cyano-piperidine MS = 208 m/e (M—CH$_2$OH)

$R_f$=0.82 (for the conditions, see Example 1).

EXAMPLE 8

2-Hydroxymethyl-3,4,5-trihydroxy-6-n-heptyl-piperidine 2.5 g (47.5% of theory) of the α-form are obtained from 3.8 g of 2-hydroxymethyl-3,4,5-trihydroxy-6-cyanopiperidine. Recrystallisation from ethanol gives small colourless prisms of melting point 144° C.; $R_f$=0.82. (For the conditions, see Example 1).

The present invention also comprises pharmaceutically acceptable bioprecursors of the active compounds of the present invention.

For the purpose of this specification the term 'pharmaceutically acceptable bioprecursor' of an active compound of the invention means a compound having a structural formula different from the active compound but which nonetheless, upon administration to an animal or human being is converted in the patient's body to the active compound.

What is claimed is:

1. A compound of the formula

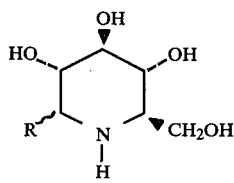

in which

R denotes C$_1$ to C$_{30}$ alkyl, C$_2$ to C$_{18}$ alkenyl or C$_2$ to C$_{18}$ alkinyl optionally substituted by 1 to 5 radicals selected from halogen, C$_1$-C$_4$-alkoxy or nitro; C$_3$ to C$_{12}$ cycloalkyl, C$_3$ to C$_{12}$ cycloalkenyl, C$_3$ to C$_{12}$ cycloalkadienyl, C$_3$ to C$_{12}$ bicycloalkyl, C$_3$ to C$_{12}$ bicycloalkenyl, C$_3$ to C$_{12}$ bicycloalkadienyl, C$_3$ to C$_{12}$ tricycloalkyl, C$_3$ to C$_{12}$ tricycloalkenyl or C$_3$ to C$_{12}$ tricycloalkadienyl; or phenyl or naphthyl being unsubstituted or having 1 to 5 substituents selected from halogen, C$_1$-C$_4$-alkyl, halogeno-C$_1$-C$_4$-alkyl, C$_1$-C$_4$-alkoxy, C$_1$-C$_4$-alkylmercapto, C$_1$-C$_4$-alkylsulphonyl, nitro, cyano, di-C$_1$ to C$_{12}$ alkylamino, di-C$_1$ to C$_{12}$ alkylaminosulphonyl or di-C$_1$ to C$_{12}$ dialkylaminocarbonyl.

2. A compound according to claim 1 in which

R denotes a C$_1$ to C$_{18}$ alkyl radical optionally substituted by 1 to 5 halogen atoms, a C$_3$ to C$_{10}$ alkenyl, C$_3$ to C$_{10}$ alkinyl, or C$_3$ to C$_7$ cycloalkyl radical or a phenyl radical which is optionally substituted by halogen, C$_1$ to C$_4$ alkyl, C$_1$ to C$_4$ alkoxy or nitro.

3. A compound of claim 1 wherein

R represents C$_1$-C$_{18}$ alkyl, C$_2$-C$_{18}$ alkenyl or C$_2$-C$_{18}$ alkinyl which is unsubstituted or substituted by 1 to 5 radicals selected from halogen, C$_1$-C$_4$-alkoxy or nitro; phenyl or naphthyl which is unsubstituted or substituted by 1 to 5 radicals selected from halogen, C$_1$-C$_4$ alkyl, halogeno C$_1$-C$_4$ alkyl, C$_1$-C$_4$-alkoxy, nitro or cyano.

4. The compound of claim 3 wherein R denotes C$_1$-C$_{18}$ alkyl, C$_3$-C$_{10}$ alkenyl, C$_3$-C$_{10}$ alkinyl.

5. The compound of claim 3 wherein R denotes a member selected from methyl, ethyl, propyl, butyl, pentyl, heptyl, octyl or phenyl.

6. The compound of claim 1 wherein the said alkyl, alkenyl or alkinyl radical is substituted by 1 to 5 radicals selected from halogen, C$_1$-C$_4$-alkoxy or nitro.

7. The compound of claim 1 wherein the said phenyl or naphthyl or is substituted by 1 to 5 radicals selected from halogen, C$_1$-C$_4$ alkyl, halogeno C$_1$-C$_4$ alkyl, C$_1$-C$_4$-alkoxy, nitro or cyano.

8. A compound according to claim 1 which is 2-hydroxymethyl-3,4,5-trihydroxy-6-propylpiperidine.

9. A compound according to claim 1 which is 2-hydroxymethyl-3,4,5-trihydroxy-6n-butyl-piperidine.

10. A compound according to claim 1 which is 2-hydroxymethyl-3,4,5-trihydroxy-6-n-pentyl-piperidine.

11. A compound according to claim 1 which is 2-hydroxymethyl-3,4,5-trihydroxy-6-n-octyl-piperidine.

12. A compound according to claim 1 which is 2-hydroxymethyl-3,4,5-trihydroxy-6-n-heptyl-piperidine.

13. A pharmaceutical composition containing as an active ingredient an amount effective for α-glucosidase inhibition, of a compound according to claim 1 in admixture with a solid or liquefied gaseous diluent other than a solvent of a molecular weight less than 200 except in the presence of a surface-active agent.

14. A pharmaceutical composition of claim 13 in the form of a sterile or physiologically isotonic aqueous solution.

15. A composition according to claim 13 or 14 containing from 0.1 to 99.5% by weight of the said active ingredient.

16. A medicament in dosage unit form comprising an amount effective for α-glucosidase inhibition, of a compound according to claim 1 together with an inert pharmaceutical carrier.

17. A medicament of claim 16 in the form of tablets, pills, dragees, or capsules.

18. A method of combating adiposity, diabetes and/or hyperlipaemia in warm-blooded animals which comprises administering to said animals an amount effective for α-glucosidase inhibition, of an active compound according to claim 1 either alone or in admixture with a diluent or in the form of a medicament.

19. A method according to claim 18 in which the active compound is administered orally.

20. A medicated fodder comprising a compound as claimed in claim 1 in an amount effective for reducing deposition of fat and saving feed protein together with an animal feedstuff.

21. A medicated fodder of claim 20 in the form of a premix.

22. A method of avoiding undesired deposition of fat and for achieving an increased deposition of lean meat, and for better feed utilization in warm-blooded animals which compises administering to said animals an effective amount of an active compound according to claim 1 either alone or in admixture with a diluent or in the form of a medicament.

* * * * *